United States Patent [19]

Ritzer et al.

[11] 4,390,510

[45] Jun. 28, 1983

[54] PROCESS FOR TREATING SPENT SILICON-CONTAINING REACTION MASSES TO PRODUCE HALOSILANES

[75] Inventors: Alan Ritzer, City Sand Lake, N.Y.; Bakulesh Shah, Corpus Christi, Tex.; Daniel E. Sliva, Scotia, N.Y.

[73] Assignee: General Electric Company, Waterford, N.Y.

[21] Appl. No.: 349,139

[22] Filed: Feb. 16, 1982

[51] Int. Cl.$^3$ .............................................. C01B 33/08
[52] U.S. Cl. ..................................................... 423/342
[58] Field of Search ......................................... 423/342

[56] References Cited

U.S. PATENT DOCUMENTS

| | | | |
|---|---|---|---|
| 2,380,995 | 8/1945 | Rochow | 556/472 |
| 2,380,999 | 8/1945 | Sprung et al. | 556/472 |
| 2,389,931 | 11/1945 | Reed et al. | 556/472 |
| 2,447,873 | 8/1948 | Rochow | 556/472 |
| 2,449,821 | 9/1948 | Sellers et al. | 556/472 |
| 2,488,487 | 11/1949 | Barry et al. | 556/473 |
| 2,803,521 | 8/1957 | Nitzsche et al. | 556/472 |
| 2,943,918 | 7/1960 | Pauls | 423/350 |
| 3,012,861 | 12/1961 | Ling | 427/86 |
| 3,133,109 | 5/1964 | Dotson | 556/472 |
| 4,165,363 | 8/1979 | Weigert et al. | 423/342 |
| 4,207,360 | 6/1980 | Padovani | 423/348 X |
| 4,217,334 | 8/1980 | Weigert et al. | 423/342 |
| 4,224,297 | 9/1980 | Straussberger et al. | 423/348 |
| 4,281,149 | 7/1981 | Shade | 556/472 |
| 4,307,242 | 12/1981 | Shah et al. | 556/472 |

FOREIGN PATENT DOCUMENTS 2807951 8/1979 Fed. Rep. of Germany .
2028289 3/1980 United Kingdom .

OTHER PUBLICATIONS

R. J. H. Voorhoeve, *Organohalosilanes, Precursors to Silicones*, Elsevier, 1967, pp. 137–139.

*Primary Examiner*—Paul F. Shaver

[57] ABSTRACT

Improved yields of monohydrogentrihalosilanes are achieved by contacting the residual silicon obtained from the preparation of organohalosilanes by a metal-catalyzed direct process by contacting the residual silicon simultaneously with gaseous hydrogen halide and with gaseous alkyl halide to form a residual silicon contact mass; selecting a temperature between about 200° C. and about 350° C. at which alkylation of the silicon contact mass in inhibited and at which hydrohalogenation of the silicon contact mass occurs; and heating the silicon contact mass at the selected temperature. The silicon reacts with the gaseous alkyl halide and the gaseous hydrogen halide at the selected temperature to produce improved yields of the monohydrogentrihalosilane. In preferred embodiments, monohydrogentrichlorosilane is produced by reacting residual silicon with hydrogen chloride and methyl chloride at a temperature less than the temperature at which a predominantly alkylation reaction occurs with the residual contact mass so that there is sufficient hydrohalogenation to form the monohydrogentrichlorosilane.

23 Claims, No Drawings

PROCESS FOR TREATING SPENT SILICON-CONTAINING REACTION MASSES TO PRODUCE HALOSILANES

BACKGROUND OF THE INVENTION

The present invention relates to a process for treating residual silicon powder, and more particularly to a process for the production of halosilanes from residual silicon powder.

The present commercial method for manufacturing organohalosilanes is well known and is described in U.S. Pat. No. 2,380,995 issued to Rochow. Rochow discloses the direct reaction of an organo-halide, such as methyl chloride, with silicon particles in order to produce organochlorosilane. Intermixed with such particles of silicon are particles of copper, thereby forming a reactive mass or reactive contact mass. In commercial practice this reaction is generally carried out in one of three types of equipment: the stirred bed type of reactor as described in Sellers, U.S. Pat. No. 2,449,821; the fluidized bed reactor as described in Reed et al., U.S. Pat. No. 2,389,931; or the rotary kiln.

Organotrichlorosilanes and diorganodichlorosilanes are the two basic products of the above described direct process reaction. Such compounds are utilized in the production of organopolysiloxane resins as described in U.S. Pat. Nos. 2,258,218 thru 2,258,222. Other products include organopolysiloxane fluids as described in U.S. Pat. No. 2,469,888 and U.S. Pat. No. 2,469,890 as well as the organopolysiloxane elastomers described in U.S. Pat. No. 2,448,756. Currently, it is preferred to produce the diorganodichlorosilanes commercially because they are generally utilized in producing the linear polysiloxane fluids and polymers used in the production of heat cured rubber elastomers and room temperature vulcanizable silicone rubber compositions of various types.

At a certain stage in the production of the organochlorosilanes by the direct process, the reactive mass or reactive contact mass containing silicon particles becomes less reactive, and it is desirable to replace the reactive contact mass. Thus, the spent or less reactive silicon particles are removed from the reactor, and new silicon particles are inserted therein whereupon the reaction is restarted. When the reactive contact mass becomes less reactive or spent, and it is replaced with a new batch of silicon, the less reactive or spent contact mass is generally referred to as residual silicon, residual silicon powder, residual silicon-containing contact mass or residual contact mass, and these terms are used interchangeably herein. An early solution to the problem was to discard the residual contact mass, however, there is considerable reactive silicon remaining in the residual contact mass, and it is desirable for reasons of economy and for avoiding waste disposal problems, to utilize at least some of the remaining silicon value in the residual contact mass.

Much research has been directed to finding a method for more fully utilizing the residual silicon particles in the reactor used to carry out the direct process synthesis of organochlorosilanes, such that the weight ratio of the organotrichlorosilanes (known as T) to diorganodichlorosilanes (known as D) could be maintained at a desired level for a longer period of time, thereby resulting in the maximum utilization of the silicon particles to produce diorganodichlorosilanes. In the production of organochlorosilanes by the direct process of Rochow, the weight ratio of triorganochlorosilane to diorganochlorosilane (T/D) is desirably about 0.1 during the production of organochlorosilanes and preferably not exceeding about 0.35. However, it has been found that in most commercial manufacturing operations, the ratio will be at about the 0.15 level when the reactor is started with new material, but after a period of reaction, it will rise to an excess of the 0.2 level. One of the breakthroughs in this area is the process disclosed by Dotson in U.S. Pat. No. 3,133,109. Dotson discloses that the silicon particles can be more fully utilized, and the amount of diorganodichlorosilane can be maximized by passing used particles from a fluid bed reactor through an external fluid energy mill. As an alternative to the external fluid energy mill, Dotson also discloses the passing of the used silicon particles that were recycled from the reactor through a plurality of sonic jets located at the base of the reactor to create a comminution of the particles or the breaking up of the silicon particles as a result of the particles striking each other or the walls of the reactor.

It was found that by utilizing the Dotson method there could be obtained from the same amount of silicon particles a larger amount of diorganodichlorosilane such that the ratio could be kept near the desired 0.15 level and would remain less than the 0.35 level for a longer period of time. However, it has also been found that the Dotson process causes underutilization of approximately 12 to 15 percent of the silicon which was introduced into the reactor and which must be removed as waste silicon from the process. It was generally considered that such silicon was spent or exhausted, and therefore no longer capable of being utilized. It is desirable to utilize this waste silicon to prevent the problems normally encountered in the disposal of wastes and for reasons of economy. Furthermore, it is even more desirable to find new processes which can utilize substantially all of the silicon value in residual silicon-containing contact masses after the T/D ratio has risen to an undesirable level.

In U.S. Pat. No. 4,281,149 issued to Shade, there is disclosed a process for treating silicon particles within such a silicon reactor system and thereby improving the usefulness of the silicon metal particles. The Shade process comprises a method of treating silicon particles having generally less than forty microns average diameter size whereupon such particles are abraded to remove the surface coating thereon and whereupon the abraded particles can be returned to the reactor for further utilization.

In U.S. Pat. No. 4,307,242, said patent being incorporated herein by reference, Shah and Ritzer disclose another process for recovering and recycling silicon fines in an organochlorosilane reactor system. The process described by Shah and Ritzer comprises a method for classifying direct process contact mass by particle size whereby the most highly poisoned or impure (spent) silicon particles are separated from the relatively unpoisoned silicon particles, and only such unpoisoned particles are recycled, thereby improving the usefulness of the silicon. Thus, instead of disposing the whole mass of spent silicon fines from the direct process, only a small fraction of the spent silicon fines need be disposed at any given time. In U.S. Pat. No. 4,307,242, fine effluent powder (residual contact mass or residual silicon) is directed to one or more mechanical cyclones for recovery. This fine effluent powder is generally the spent reaction mass from a reactor which produces organotrichlorosilane and diorganodichlorosilane products. Crude T and D products are recovered from the top of the cyclones and these products may contain small amounts of "very fine" entrained particles therein. The remainder of the reaction mass is treated pneumatically in the mechanical cyclones and is directed to a receiving hopper for alternate disposition. It is desirable to obtain useful products at any stage described by Shah and Ritzer, and especially from the relatively unpoisoned fraction of secondary cyclone fines resulting from the classifying process of U.S. Pat. No. 4,307,242. It is also desirable to obtain useful products from silicon and residual silicon-containing contact masses obtained from any other source.

One such useful product which can be obtained from various reactions with silicon, is trichlorosilane also designated herein as monohydrogentrichlorosilane ($HSiCl_3$). A study on the effect of HCl on the synthesis of methylchlorosilanes is reported on page 138 in Voorhoeve, *Organohalosilanes, Precursors to Silicones*, published by Elsevier in 1967. Voorhoeve reported reactions carried out with metallurgical grade silicon in the presence of a copper catalyst with various molar ratios of methyl chloride:hydrogen chloride ranging from 6:1 to 1:6. However, these reactions were all carried out at 300° C., and there is no report of any temperature selectivity effect by Voorhoeve.

Barry et al. in U.S. Pat. No. 2,488,487, found increased yields of the "more valuable monoalkyl silicon halides" by the simultaneous introduction of a hydrogen halide, e.g. HCl, along with an alkyl halide upon contact with silicon or an alloy or mixture of silicon with metal at an elevated temperature. Although Barry et al. report a temperature range of 200° C. to 550° C., they found that admixture of hydrogen chloride with the starting methyl chloride resulted in increased yields of monomethyl silicon chlorides, and there is no report of improved or high yields of monohydrogentrihalosilane or of any temperature selectivity effect.

In a method of treating spent metallic reaction masses from the direct process production of organohalosilanes, Nitzche et al. in U.S. Pat. No. 2,803,521, report that the reaction of methyl chloride and silicon at 200° C. to 500° C., usually in the presence of copper or copper chloride, and often with HCl as an added reactant, is the best known and most widely used commercial application of the direct process. According to Nitzche et al., this particular reaction produces various methylchlorosilanes, such as, $CH_3SiCl_3$, $(CH_3)_2SiCl_2$, $(CH_3)_3SiCl$ and $CH_3HSiCl_2$. However, Nitzche et al. treat spent (residual) silicon-containing reaction masses by dispersing the reaction mass in water or dilute hydrochloric acid and contact the dispersed mass with a chloride source at a temperature of from 20° C. to 100° C. The silicon particles settle and are separated from the supernatant, and the metal salts in the supernatant solution are precipitated, collected and re-used as fresh catalyst. Nitzche et al. do not suggest preparing monohydrogentrichlorosilane from the spent metallic reaction mass, nor do they report any temperature selectivity effect.

Among the well-known uses for trichlorosilane is a hydrosilation reaction of trichlorosilane (monohydrogentrichlorosilane) to make organofunctional silanes, and the use of trichlorosilane as a feedstock in the manufacture of hyper-pure silicon as discussed in U.K. Patent Application GB 2,028,289 published Mar. 5, 1980 by Woerner et al. Recent developments in the semi-conductor industry have created a growing demand for low-cost, hyper-pure silicon for electronic devices, photovoltaic solar cells and the like. Woerner et al. further indicate that trichlorosilane and silicon tetrachloride are made by the reaction of silicon and hydrogen chloride. Furthermore, Rochow in U.S. Pat. No. 2,380,995 reports the reaction of hydrogen chloride with silicon as described by Combes in Compt. rend. 122, 531 (1896) wherein a mixture of about 80% trichlorosilane and 20% silicon tetrachloride were obtained by passing hydrogen chloride through an iron tube filled with silicon heated to 300° C. to 440° C. Thus, it is desirable to provide additional sources for trichlorosilane, to provide economical methods of making trichlorosilane and to provide a synthesis for making trichlorosilane wherein the yield of trichlorosilane is improved. It is also desirable to provide improved methods of managing residual silicon-containing contact mass obtained from the preparation of organohalosilanes by the direct process reaction.

SUMMARY OF THE INVENTION

Accordingly, it is the primary object of the present invention to provide a process for utilizing residual silicon obtained from the preparation of organochlorosilanes.

It is another object of the present invention to provide an improved process for obtaining trichlorosilane from silicon.

Another object of the present invention is to provide a process for preparing trichlorosilane from residual silicon contact masses.

Still another object of the present invention is to provide a method for improving the amount of monohydrogentrihalosilane (trihalosilane) obtained from the reaction of silicon with alkyl halide in the metal-catalyzed direct process.

Another object of the present invention is to provide a method for improving the yield of monohydrogentrichlorosilane (trichlorosilane) obtained from residual silicon-containing contact mass obtained from the preparation of organochlorosilanes by metal-catalyzed direct process reactions.

Other objects and advantages of the invention will become apparent from the following detailed description.

In accordance with the objects of the present invention, monohydrogentrihalosilanes are prepared from the residual silicon obtained from the preparation of organohalosilanes by a metal-catalyzed direct process, comprising, contacting the residual silicon simultaneously with gaseous hydrogen halide and with gaseous alkyl halide to form a residual silicon contact mass and heating the residual silicon contact mass at a temperature less than the temperature at which substantial alkylation of the residual silicon contact mass occurs, whereby the residual silicon reacts at said temperature to produce reaction products containing monohydrogentrihalosilanes. In accordance with the present invention, the selection of the temperature at which the residual silicon contact mass is heated, is critical, and it must be a temperature at which alkylation of the silicon contact mass is inhibited or retarded and at which hydrohalogenation of the residual silicon contact mass is promoted. Generally, the temperature at which the hydrohalogenation of the silicon in the residual silicon contact mass occurs, is between about 200° C. and about 350° C. The temperature selectivity may be alternatively expressed as the temperature less than the temperature at which substantial alkylation of the residual silicon contact mass occurs.

In accordance with at least some of the objects of the present invention, there is also described a method for improving the amount of monohydrogentrihalosilane obtained from the reaction of silicon with alkyl halide in the metal-catalyzed direct process, comprising, contacting the silicon simultaneously with gaseous alkyl halide and with gaseous hydrogen halide to form a silicon contact mass; selecting a temperature between about 200° C. and about 350° C. at which alkylation of the silicon contact mass is inhibited or retarded and at which hydrohalogenation of the silicon contact mass occurs or is promoted; and heating the silicon contact mass at the selected temperature, whereby the silicon reacts with the gaseous alkyl halide and the gaseous hydrogen halide at the selected temperature to produce improved yields of monohydrogentrihalosilane.

By co-feeding gaseous hydrogen chloride and gaseous methyl chloride to a residual silicon contact mass, it has been demonstrated by the process of the present invention that the alkylation reaction between the methyl chloride and silicon is suppressed when the reaction is carried out at selected reduced temperatures. Although there is some sacrifice in the silicon utilization by using the process of the present invention as compared to the silicon utilization of a reaction between metallurgical grade silicon and gaseous hydrogen chloride in the absence of methyl chloride, the process of the present invention remains desirable in those cases where methyl chloride sources are readily available. However, it has been demonstrated that there is increased silicon utilization by the process of the present invention over the silicon utilization realized when methyl chloride is used in the absence of hydrogen chloride. It has also been found that silicon tetrachloride as well as monohydrogentrichlorosilane is produced along with various methyltrichlorosilanes. However, by selecting a reduced operating temperature, suppression of the production of methylchlorosilanes by suppression of alkylation has been achieved while promoting the hydrochlorination reaction to produce monohydrogentrichlorosilane.

DETAILED DESCRIPTION OF THE INVENTION

The present invention relates to a process for improving the yield of monohydrogentrihalosilanes ($HSiX_3$) wherein X is a halogen, when silicon and especially residual silicon obtained from the preparation of organohalosilanes by a metal-catalyzed direct process, is reacted with gaseous alkyl halide in the presence of gaseous hydrogen halide. Heretofore, the reaction has been a substantially alkylation reaction of the residual silicon resulting in the production of alkyl silicon halides accompanied by only minor amounts of hydrohalogenation. In accordance with at least some of the objects of the present invention, and by controlling the temperature, namely, by carrying out the reactions at lower selective tempetures, the yield of the monohydrogentrihalosilane is substantially improved, and in certain embodiments, the product is predominantly monohydrogentrihalosilane. To achieve the improved yields of monhydrogentrihalosilanes, temperature selectivity is critical, and the silicon or residual silicon contact mass is heated at a temperature less than the temperature at which substantial alkylation of the silicon or residual silicon contact mass occurs.

The predominantly alkyl silicon halide products resulting from the alkylation of the silicon are clearly illustrated by Barry et al. in U.S. Pat. No. 2,488,487 and by Nitzsche et al. in U.S. Pat. No. 2,803,521. The results of alkylation and hydrohalogenation by contacting metallurgical grade silicon with methyl chloride and hydrogen chloride in varying ratios at a constant temperature are also illustrated by Voorhoeve in a reference discussed above. It can be seen by reviewing the disclosure and examples of Barry et al. that without using temperature selectivity, the alkylation of the silicon is the predominant reaction when methyl chloride and hydrogen chloride contact silicon in the presence of a metal catalyst at elevated temperatures. Nitzsche et al. also disclose the various methylchlorosilanes obtained from the reaction of methyl chloride and silicon at 200°–500° C. in the presence of copper and hydrogen chloride as an added reactant. By the process of the present invention, the alkylation reaction is suppressed, inhibited or retarded while the hydrohalogenation reaction is promoted by carefully choosing and controlling the temperature of the reaction. Voorhoeve has illustrated that this phenomenon can also occur by altering the molar ratio of methyl chloride to hydrogen chloride while maintaining a constant temperature at 300° C. Thus, by increasing the amount of hydrogen chloride, Voorhoeve has illustrated that the amount of trichlorosilane in the product increases while the amount of various methylchlorosilanes decreases.

When methyl chloride is used as the gaseous alkyl halide and hydrogen chloride is used as the gaseous hydrogen halide, and the reaction is carried out by means of the direct process using an appropriate catalyst, such as, copper, the product generally comprises silicon tetrachloride ($SiCl_4$), monohydrogentrichlorosilane, otherwise referred to herein as trichlorosilane ($HSiCl_3$), methylhydrogendichlorosilane ($CH_3HSiCl_2$), methyltrichlorosilane ($CH_3SiCl_3$), dimethyldichlorosilane (($CH_3)_2SiCl_2$), trimethylchlorosilane (($CH_3)_3SiCl$) and residue generally made up of several components including hexachlorodisilane ($Cl_3Si-SiCl_3$) and various siloxanes. The residue is generally characterized as the high boiling fraction and includes any component having a boiling point greater than 70° C. As expressed above, in accordance with the process of the present invention, and in the preferred embodiment wherein the gaseous alkyl halide is methyl chloride and the gaseous hydrogen halide is hydrogen chloride, the desired product is monohydrogentrichlorosilane.

In the preferred embodiments of the process of the present invention, the silicon is a residual silicon, such as, a residual silicon-containing contact mass obtained from the direct process synthesis or preparation of organochlorosilanes which uses a metal catalyst in the reaction. In the process of the present invention, the residual silicon is one which contains a metal catalyst by virtue of its being the spent contact mass from the direct process which utilizes a metal catalyst, or a metal catalyst may be added to the silicon contact mass if there is not metal catalyst therein, or if it is desirable to supplement insufficient amounts of metal catalyst in the residual contact mass. Generally, in accordance with the process of the present invention, the residual silicon-containing contact mass may contain other adjuvants and additives which had been added during the direct process reaction, or additives and adjuvants which do not interfere with the process of the present invention may be added to promote the hydrohalogenation reaction or for any other suitable purpose.

The direct process synthesis or preparation of organosilanes is described above and in U.S. Pat. No. 2,380,995 issued to Rochow. The present invention may be carried out without further treatment of the residual silicon-containing contact mass remaining, for example, after the direct process synthesis of Rochow. However, in the preferred embodiments, the residual silicon-containing contact mass is further treated to remove any parts of the residual contact mass which poison or interfere with the hydrohalogenation reaction, e.g., by comminution, separation, treatment with agents to dissolve or extract non-reactive substances, and the like. In one preferred embodiment, the residual silicon-containing contact mass obtained by the direct process synthesis may be subjected to the process disclosed in U.S. Pat. No. 4,307,242 issued to Shah and Ritzer. According to the Shah and Ritzer process, which is incorporated herein by reference, a silicon-containing contact mass referred to as "effluent contact mass powder", or alternatively referred to as "silicon fines", is directed to an aerodynamic centrifugal classifier. Such a classifier is an apparatus capable of classifying and segregating the cyclone fines into discrete fractions according to particle size. In the most general case, relatively coarse fines are recycled to the organochlorosilane reactor, and the finest fraction is discarded or otherwise disposed. However, according to U.S. Pat. No. 4,307,242, the so-called finest fraction contains the predominantly highest percentages of non-silicon impurities, and a determination must be made as to which size fraction will be discarded and which will be recycled. Thus, in a process for purifying silicon metal contact mass from a direct process organohalosilane reactor system according to U.S. Pat. No. 4,307,242, a portion of reactor contact mass is analyzed for particle size distribution; the analyzed contact mass is classified into a relatively pure first fraction and a relatively impure second fraction; and the first and second fractions are segregated. The silicon fines or effluent contact mass powder can be collected in a secondary cyclone and are passed into a receiving hopper and thereafter into a transfer hopper from which the silicon fines pass to a mechanical classifier which is preferably an aerodynamnic or centrifugal classifier. These fines are defined herein as the silicon fines collected from a secondary cyclone used to separate spent silicon fines obtained from the direct process manufacture of organochlorosilane. In preferred embodiments of the present invention, the relatively pure, classified second cyclone fines are contacted simultaneously with gaseous hydrogen halide, such as hydrogen chloride, and with gaseous alkyl halide, such as methyl chloride, to form a residual silicon contact mass; a temperature between about 200° C. and about 350° C. at which alkylation of the residual silicon-containing contact mass is inhibited or retarded and at which hydrohalogenation of the residual silicon-containing contact mass is promoted, is selected; and the residual silicon-containing contact mass is heated at the selected temperature, whereby the silicon reacts with the gaseous alkyl halide and the gaseous hydrogen halide at the selected temperature to produce improved yields of monohydrogentrihalosilane.

In another embodiment, the source of residual silicon is the comminuted particles of silicon taken from the process and apparatus described by Dotson in U.S. Pat. No. 3,133,109 which is incorporated herein by reference. Dotson passes used particles containing silicon from a fluid bed reactor through an external fluid energy mill or passes them through a plurality of sonic jets located at the base of the reactor to create a comminution of the particles or the breaking up of the silicon particles as a result of the particles striking each other or the walls of the reactor. Thus, any residual silicon-containing contact mass which has been crushed, pulverized or disintegrated by breakage of individual particles of the silicon-containing mixture from compression, impact, grinding, attrition or the like, may be used in the process of the present invention.

In certain instances, it may be possible to use a virgin silicon powder which has never been used in a process such as those described above, as the source of silicon. Thus, any finely-divided silicon, preferably free from any contaminants which can cause contamination of the ultimate product, may be used in the process of the present invention in conjunction with a suitable catalyst such as the catalyst well-known in the prior art.

The size of any silicon or residual silicon particles which may be used in the process of the present invention, is not critical, and the silicon or residual silicon may be in any finely-divided form, and for optimum results, the silicon in the reactor generally has an average particle diameter in the range of from about 20 microns to about 200 microns. Preferably, at least 25% by weight of the silicon particles have actual diameters in the range of from about 20 microns to about 200 microns. As discussed above, a wide variety of silicon alloys, residual silicon alloys, or corresponding silicon or residual silicon and metal mixtures may be used in the process of the present invention. Examples of silicon alloys or mixtures which may be used include calcium-silicon alloys, calcium-manganese-silicon alloys, manganese-zirconium-silicon alloys, iron-silicon alloys, titanium-silicon alloys, zirconium-silicon alloys, copper-silicon alloys, intimate mixtures of silicon with copper, nickel, tin or silver and the like.

Although there is no limitation upon the apparatus or device in which the process of the present invention can be carried out, the apparatus or device must be one wherein the silicon or residual silicon can be adequately contacted with the alkyl halide and the hydrogen halide and maintained or controlled at the temperature or temperatures selected for the hydrohalogenation reaction. The reactor or reaction chamber may be of any suitable size or shape and is preferably made of a material which will not be corroded by or enter into a reaction with the reactants and the products and/or by-products. The apparatus or device must be capable of heating the silicon or silicon-containing contact mass at the critical temperature or within a critical temperature range as discussed above. The process of the present invention may be carried out continuously, intermittently or by batch-wise means. Any suitable prior art techniques may be utilized to carry out the process.

One procedure for carrying out the process of the present invention comprises conducting the alkyl halide admixed with the hydrogen halide over and through a stationary bed of residual silicon maintained at the selective temperature at which alkylation is retarded or inhibited and hydrohalogenation is promoted. In another mode, the process may be carried out by simultaneously passing vapors of the alkyl halide and hydrogen halide through a rotating externally heated tumbler containing the residual silicon while maintaining the heated tumbler at the selective temperatures. Still another mode of carrying out the process of the present invention consists in preheating the vapor mixture to the selective temperature at which hydrohalogenation is promoted and alkylation is inhibited before contacting the residual silicon.

The introduction of the gases and/or vapors into the reaction chamber is not critical, and the hydrogen halide gas and alkyl halide gas or vapor may be admixed prior to introducing them into the reaction chamber or vessel, or they may be introduced into the reaction chamber or vessel separately. Any conventional metering and/or measuring means may be used to provide a suitable ratio of the gases in the reaction chamber or vessel. It is also within the scope of the present invention to feed multiple streams of the gases into the reactor. In one preferred embodiment, the process is carried out by forming a fluidized bed of the residual silicon or silicon, and the residual silicon or silicon is contacted by the appropriate gases or vapors while the residual silicon or silicon is in the fluidized bed mode. Various embodiments for maintaining a fluidized bed of the residual silicon can be used and include the use of a gas or vapor velocity sufficient to maintain the residual silicon in a fluidized state within the reactor. This may be accomplished by injecting the alkyl halide and/or hydrogen halide into the particulate residual silicon at a suitable velocity to fluidize the particulate matter. An optimum velocity of the gas and/or vapors may be determined by one skilled in the art and depends upon various operating conditions. When a stirred bed reactor is used, or when a rotary kiln is used, the gas velocity or flow rate can be below the minimum velocity required for fluidization of the silicon in the reastor, and can more precisely reflect the stoichiometric amount of hydrogen halide and alkyl halide required to react with the silicon. Naturally, other conventional fluidizing means may be used to maintain the bed of residual silicon in a fluidized state while it is being contacted with the alkyl halide and the hydrogen halide, and it is also within the scope of the present invention to utilize a combination of means for maintaining the bed of residual silicon in a fluidized state. Although it is not generally desired because it necessitates heavy venting means, it is possible to use an inert gas, for example, nitrogen, to fluidize, or to supplement other means of fluidizing, the residual silicon-containing contact mass. A conventional fluidized bed reactor is described by Reed et al. in U.S. Pat. No. 2,389,931. Other alternative means for contacting the residual silicon with the gaseous materials include a stirred bed type of reactor as described by Sellers in U.S. Pat. No. 2,449,821 or by means of a conventional rotary kiln. Means for heating the bed of residual silicon in the reactor and maintaining the bed of residual silicon at the selective temperature at which the hydrohalogenation reaction is promoted and the alkylation reaction is inhibited, may also be provided by any conventional means, and both internal and external sources of heating, and/or cooling including the heating of the gases and/or vapors, may be used in the process of the present invention. The foregoing references provide examples of conventional means for heating the beds contained therein.

In the preferred embodiment of the present invention, the alkyl halide is methyl chloride ($CH_3Cl$). Generally, the alkyl halides which may be used in the process of the present invention include those having the formula $R_nH_{2n+1}X$ wherein X is halogen, and n is an integer from 1 to 4. The alkyl group having from 1 to 4 carbon atoms may be a straight or branched chain. The halogen may be chloride, bromide, iodide or fluoride. In the process of the present invention, a single alkyl halide may be used in the reaction or a mixture of alkyl halides may be used in the reaction.

The preferred hydrogen halide which may be used in the process of the present invention is hydrogen chloride. However, in various embodiments, hydrogen bromide, hydrogen iodide or hydrogen fluoride may be used as the hydrogen halide. It is also possible to use mixtures of hydrogen halides in the process of the present invention.

The amount or proportions of hydrogen halide and of alkyl halide used in the process of the present invention is not critical. Usually from 0.5 to 20 parts by volume of the hydrogen halide are employed per part of the vaporized alkyl halide, but the hydrogen halide may be used in greater or smaller proportions as desired. In certain embodiments, the molar ratio of alkyl halide to hydrogen hallide is in the range of about 6:1 to about 1:6. However, in certain preferred embodiments, the molar ratio of alkyl halide to hydrogen halide is in the range of about 3:1 to about 1:3. In one preferred embodiment of the present invention, when the alkyl halide is methyl chloride, and when the hydrogen halide is hydrogen chloride, the molar ratio of methyl chloride:hydrogen chloride is about 3:1. As discussed above, it has been reported by Voorhoeve that as the amount of hydrogen chloride increases, the amount of trichlorosilane increases in the reaction of hydrogen chloride and methyl chloride with silicon at a temperature of 300° C. in the presence of a copper catalyst.

The rate of gas or vapor flow in the process of the present invention is not critical, however, in preferred embodiments, it is controlled so as to cause consumption of about 0.5 or more of the alkyl halide in a single passage through the bed of residual silicon. Since it is sometimes difficult to attain a high conversion in a single pass, in which case a considerable portion, for example, from about 0.5 to about 0.8, of the vapors flowing from the bed may be recirculated through the bed so as to cause further consumption of the alkyl halide. Such recirculation of the vapors is of further advantage in that it renders more nearly uniform the temperature throughout the reaction zone, and it tends to cause the reaction to take place throughout a large portion of the residual silicon-containing bed rather than in localized portions of the bed. While operating in this mode, a portion of the vapors flowing from the residual silicon bed, that is flowing from the reactor, may be withdrawn from the reaction system and cooled to condense any product therein. The operation may be continued until the silicon in the residual silicon is consumed to the point desired. As explained above, batch-wise modes are also possible, and in certain cases the reactor can be initially charged with the gaseous alkyl halide and hydrogen halide and maintained at the desired selective temperature until the reaction is complete. Completion of the reaction or substantial completion of the reaction can be determined easily by the product analysis discussed in more detail below.

As discussed above, the temperature of the reaction of the alkyl halide and hydrogen halide with the residual silicon is critical and must be selectively made to achieve the desired hydrohalogenation of the silicon. The residual silicon contact mass, that is, the residual silicon in the presence of the hydrogen halide and alkyl halide, is heated selectively at a temperature in the range of about 200° C. to about 350° C. depending upon the variables of the process. Thus, to achieve the improved yields of monohydrogentrihalosilanes in accordance with the process of the present invention, the residual silicon contact mass is heated in the presence of the gaseous hydrogen halide and gaseous alkyl halide at a temperature less than the temperature at which substantial alkylation of the silicon occurs or is promoted. Generally, in preparing monohydrogentrichlorosilane, the residual silicon is heated in the presence of methyl chloride and hydrogen chloride at a temperature between about 200° C. and about 350° C., the temperature being less than the temperature at which substantial alkylation of the residual silicon occurs and at a temperature wherein substantial hydrohalogenation of the silicon occurs. Generally, it is considered that substantial hydrohalogenation has been reached when about 15% by weight, as determined by gas chromatography, of the product is monohydrogentrihalosilane. Generally, it is considered that alkylation is substantial when the distribution of organohalosilanes in the product totals about 70% by weight or more as determined by gas chromatography. Thus, in improving the amount of monohydrogentrihalosilane in the reaction product between silicon in residual silicon contact mass and alkyl halide and hydrogen halide, a temperature must be selected between about 200° C. and about 350° C. at which alkylation of the silicon contact mass is inhibited and at which hydrohalogenation of the silicon contact mass occurs, and the silicon contact mass is heated at the selected temperature whereby the silicon reacts with the gaseous alkyl halide and the gaseous hydrogen halide at the selected temperature to produce improved yields of the monohydrogentrihalosilane.

Temperature selectivity can be easily determined by product analysis by monitoring either the product stream, the gas recirculation stream, the gas in the reaction chamber and the like, by gas chromatography or by any equivalent means for measuring the composition of gases. This monitoring of the appropriate stream or chamber may be intermittent or continuous, and it may be carried out by conventional equipment, devices and techniques well-known in the art. When the alkylation reaction occurs, and the organohalosilanes appear in undesirable quantities, that is, in substantial amounts in the monitored stream or chamber, the temperature is lowered to suppress alkylation and to promote hydrohalogenation of the silicon in the residual silicon mass. Furthermore, in certain instances, it may be necessary to control the temperature within a range which suppresses alkylation and which promotes hydrohalogenation. For example, when the reaction becomes exothermic after it has been initiated, it may be desirable to control the temperature within a range which suppresses the alkylation of the silicon and which promotes the hydrohalogenation of the silicon. This also can be determined by monitoring the gases in the streams and/or chambers as described above, and appropriate measures can be taken to terminate heating and/or to provide conventional cooling to maintain the selective temperature. From the foregoing discussion, it will be evident that the selective temperature may also embrace a temperature range within which the alkylation reaction is suppressed and the hydrohalogenation reaction is promoted.

Certain variables which will effect the reaction between the silicon in the residual silicon contact mass with the alkyl halide and hydrogen halide include the particular alkyl halide and hydrogen hallide employed as the starting material and the conditions under which the reaction is conducted, such as the time of contact of the reactants, the quality and particle size of the silicon, and the like. Furthermore, the rate constant, K, differs for each reaction and under varying conditions, and this has an effect upon the temperature selectivity, although, as a practical matter, the temperature selectivity is most easily determined for any set of reaction conditions, reactants, reactor equipment and the like, by monitoring the product gases as described above.

The reaction is usually carried out at atmospheric pressure, however, lower or much higher pressures, for example, pressures as high as 2000 lbs. per square inch may be employed. Diluents, such as carbon dioxide, carbon monoxide, silicon tetrachloride, nitrogen, and various other inert gases, may also be added as desired.

The products formed by the process of the present invention may be collected and separated by conventional devices and processes. Thus, the product from the reaction of the present invention may be suitably collected and the monohydrogentrichlorosilane may be separated therefrom by any suitable technique. One mode of collection is by condensation in a conventional condenser cooled to about $-20°$ C. with an appropriate coolant, for example, a methanol-based coolant. This causes the monohydrogentrichlorosilane, silicon tetrahalide, organohalosilanes and other by-products and residue to condense. They are appropriately collected, and may thereafter be separated by any suitable separation technique, including fractional distillation.

Generally, it is desirable to carry out the process of the present invention under anhydrous conditions to prevent the formation of hydrolysis by-products and other undesirable by-products which deplete the yield of the monohydrogentrihalosilanes. Accordingly, in preferred embodiments, steps may be taken to exclude moisture from the system and from the reactants.

EXAMPLES

The following examples are illustrative of the present invention and are not in any way intended to limit the scope of the invention:

A one-inch (2.54 cm.) electrically heated, stirred-bed reactor of stainless steel construction consisting of a tube 2.54 cm. in diameter and 45.7 cm. (18 inches) in length equipped with specific flange end-plugs and an electricaly motor driven discontinuous helical spiral stirrer for bed agitation was used as a reactor. The tube section was divided into an upper and a lower reaction zone, each reaction zone being fitted with an independent heater to maintain the zones at the desired temperature settings. The reactor barrel or tube was sufficiently insulated to prevent heat loss and heat vibrations. An inlet was provided in the bottom of the tube to provide for the source of gases and/or vapors, that is, to provide for the alkyl halide and hydrogen halide. An outlet was provided at the top of the tube and equipped with a suitable condenser to provide for the collection of the liquid trichlorosilane product and any by-products and a suitable vent for the venting of gas. Suitable glass and plastic connectors and tubes were used to minimize the corrosive effect of the reaction gases. For these examples the reactions were carried out in a batch mode.

The residual silicon-containing contact mass used in the following examples consisted of secondary cyclone fines described above in the process disclosed and claimed by Shah and Ritzer in U.S. Pat. No. 4,307,242. The residual silicon secondary cyclone fines were analyzed and contained approximately 2.1 weight percent carbon, 3.8 weight percent copper, 2.7 weight percent iron, 1.7 weight percent aluminum, 1.0 weight percent zinc, 69.0 weight percent silicon and a balance of chlorine, hydrogen and trace quantities of other elements. The designated quantity of secondary cyclone fines were placed in the stirred-bed reactor system described above. The reaction zone temperature was maintained at the selected temperature for the duration of the experiment. Methyl chloride and/or anhydrous hydrogen chloride were metered into the reaction zone at the rates shown for each example via linear mass flow meters. The reactions were carried out at three temperatures, namely, 300° C., 250° C. and 200° C. Prior to the reaction study, the reactor internal temperature profile was established under nitrogen flow using a thermocouple probe. In this manner, temperature controller settings were determined. Under reaction conditions, reactor external temperatures (both reaction and upper zones) were monitored continuously.

The methyl chloride reactant flow was standardized using a rotameter-linear mass flow meter in series. Hydrogen chloride co-feeds were accomplished using a linear mass flow meter with appropriate correction factor.

Reaction rates were determined by recovery of crude product per unit time. Methylchlorosilane crudes (crude fractions) were corrected, that is, normalized, for unreacted methyl chloride based on gas chromatography analysis. Silicon utilization was computed by subtraction of silicon consumed to form product from initial silicon level as determined by alkali fusion method of contact mass sample. Any appropriate silicon analysis may be utilized for this purpose.

Crude product distributions were determined by gas chromatography. Residue or high boiling fraction content was also determined by gas chromatography. For the cases of comparative overall material yields with methyl chloride, hydrogen chloride or mixed methyl chloride/hydrogen chloride feeds at varied temperatures, contact masses were reacted until exhaustion, that is, until there was no additional crude product formation.

EXAMPLE 1

A sample of the secondary cyclone fines described above weighing 50.0 grams was placed in the reactor described above, and anhydrous hydrogen chloride was fed into the reactor at 100 SCCM. The reactor was maintained at ambient pressure and heated at 300° C. The product was analyzed as described above, and about 76% of the silicon in the secondary cyclone fines was converted to product of which about 94.4% consisted of trichlorosilane and silicon tetrachloride. About 4.6% by weight of effluent was considered high-boiling residue, that is, it had a boiling point greater than 70° C., of which about one-half was hexachlorodisilane. The results are shown for comparative purposes in Tables 1 and 2 below.

EXAMPLE 2

All reaction conditions and quantities were the same in this example as reported in Example 1 except the stirred bed reactor was maintained at 250° C. at ambient pressure. The analytical data for this example is shown in Tables 1 and 2 below.

EXAMPLE 3

Reaction conditions and quantities were the same in this example as reported in Example 1 except the stirred bed reactor was maintained at 200° C. at ambient pressure. The data for this example is reported in Tables 1 and 2 below.

EXAMPLE 4

Residual silicon secondary cyclone fines taken from the same batch as the preceeding examples were reacted in the same stirred bed reactor system as described for Examples 1-3 above using a methyl chloride gaseous feed at 300° C. and ambient pressure as in Example 1 above. No anhydrous hydrogen chloride was used in this example. About 36% silicon utilization was achieved with about 92% of the effluent consisting of methyltrichlorosilane and dimethyldichlorosilane; 2.6% by weight of the product was high boiling residue of which about 85% by weight was 1,1,2-trichlorotrimethyldisilane and 1,1,2,2-tetrachlorodimethyldisilane. The data from this example is reported in Tables 1 and 2 below.

EXAMPLE 5

Another identical sample of secondary cyclone fines was treated in accordance with the process of Example 4 except the reaction was carried out at 250° C. at ambient pressure. The data from this example is reported in Tables 1 and 2 below.

EXAMPLE 6

Residual silicon secondary cyclone fines weighing 50.0 grams and taken from the same batch as the foregoing examples was reacted in the same reactor system at 300° C. and ambient pressure employing both methyl chloride gas and anhydrous hydrogen chloride gas such that the total molar throughput of gas per unit time was identical to that of the foregoing examples. The gases were metered to achieve a 3:1 molar ratio of methyl chloride:hydrogen chloride distribution. Overall, about 64% silicon utilization was achieved. About 22 percent by weight of the effluent was silicon tetrachloride and trichlorosilane combined; about 59 percent by weight of the effluent was methyltrichlorosilane and dimethyldichlorosilane combined; and the balance consisted predominantly of about 12 weight percent methylmonohydrogendichlorosilane, about 2.5 percent by weight trimethylchlorosilane, and about 3.1 percent by weight residue and dimethylmonohydrogenchlorosilane. The data for this example is reported in Tables 1 and 2 below.

EXAMPLE 7

Reaction conditions and quantities were identical to that reported in Example 6 above except the reaction temperature was 250° C. at ambient pressure. Overall silicon utilization was 50 percent. The data for this example reported in Tables 1 and 2 below, demonstrates that the utilization of silicon to desirable products, trichlorosilane and silicon tetrachloride, was approximately double via reduction of reaction temperature, that is, 13.2% at 300° C. and 25.5% at 250° C.

EXAMPLE 8

Reaction conditions and quantities were identical to those of Examples 6 & 7 above except a reaction temperature of 200° C. was used in this example. Overall silicon utilization was 31%. The data for this example is reported in Tables 1 and 2 below.

TABLE 1

SUMMARY OF PRODUCTS AT VARIOUS SELECTED TEMPERATURES

| Example No. | Feed Gas | Reaction Temp. °C. | $^2$A | $^3$B | $^4$C | $^5$D | $^6$E | $^7$F |
|---|---|---|---|---|---|---|---|---|
| 1 | HCl | 300 | 68.08 | 26.38 | 0.10 | Trace | 0.58 | 0.11 |
| 2 | HCl | 250 | 69.82 | 25.63 | 0.04 | Trace | 0.28 | 0.10 |
| 3 | HCl | 200 | 74.20 | 16.39 | 0.01 | Not Determined | 0.06 | 0.09 |
| 4 | $^1$MeCl | 300 | Trace | Trace | 1.07 | 3.73 | 19.66 | 71.88 |
| 5 | $^1$MeCl (3:1) | 250 | Trace | Trace | 0.15 | 3.49 | 10.83 | 80.14 |
| 6 | MeCl:HCl (3:1) | 300 | 16.27 | 5.39 | 12.39 | 2.48 | 36.37 | 22.85 |
| 7 | MeCl:HCl (3:1) | 250 | 38.13 | 10.89 | 8.32 | 0.67 | 20.57 | 14.33 |
| 8 | MeCl:HCl | 200 | 64.17 | 13.97 | 2.81 | Trace | 9.21 | 1.36 |

$^1$MeCl represents methyl chloride
$^2$A is trichlorosilane (HSiCl$_3$)
$^3$B is silicon tetrachloride (SiCl$_4$)
$^4$C is methyldichlorosilane
$^5$D is trimethylchlorosilane
$^6$E is methyltrichlorosilane
$^7$F is dimethyldichlorosilane

TABLE 2

SUMMARY OF REACTION CONDITIONS AND PRODUCT RATIOS

| Example No. | Feed Gas | Reaction Temp. °C. | Overall % Si Utilization | % Si Utilized For Product A+B$^2$ | % Si Utilized For MCS's* | $^2$B/A | $^2$E/F | % R** |
|---|---|---|---|---|---|---|---|---|
| 1 | HCl | 300 | 76.5 | 72.3 | 0.60 | 0.39 | — | 4.60 |
| 2 | HCl | 250 | 77.7 | 74.2 | 0.33 | 0.37 | — | 4.05 |
| 3 | HCl | 200 | 64.2 | 58.0 | 0.10 | 0.22 | — | 9.16 |
| 4 | $^1$MeCl | 300 | 38.2 | — | 36.8 | — | 0.27 | 2.94 |
| 5 | $^1$MeCl (3:1) | 250 | 38.4 | — | 36.3 | — | 0.14 | 5.39 |
| 6 | MeCl:HCl (3:1) | 300 | 78.1 | 16.9 | 57.8 | 0.33 | 1.59 | 3.08 |
| 7 | MeCl:HCl (3:1) | 250 | 58.6 | 28.7 | 25.7 | 0.29 | 1.44 | 6.45 |
| 8 | MeCl:HCl | 200 | 33.6 | 26.3 | 4.5 | 0.22 | 6.77 | 8.06 |

*MCS's represents the methylchlorosilanes
**R represents residue (fraction boiling greater than 70° C.)
$^1$MeCl represents methyl chloride
$^2$A, B, E and F are defined in Table 1

From the foregoing data it can be seen that the residual silicon secondary cyclone fines and hydrogen chloride react readily at 300° C., 250° C. and 200° C. to generate predominantly trichlorosilane and silicon tetrachloride. At comparable temperatures, reaction with hydrogen chloride results in considerably higher silicon utilization as opposed to reaction with methyl chloride (even at 200° C.). While decreasing the temperature from 300° C. to 250° C. results in no effect on overall silicon utilization in terms of reaction with methyl chloride or hydrogen chloride exclusively, there were marked selectivity differences in the lower temperature methyl chloride reaction, namely, a sharply lower overall batch E/F, a reduced methyl monohydrogendichlorosilane formation and increased residue formation. A reactant co-feed as exemplified by 3:1 methyl chloride:hydrogen chloride (molar ratio) shifted the results as follows:

(a) at 250° C., while overall silicon utilization was lower than the 100% hydrogen chloride mode, it was higher than the 100% methyl chloride mode.

(b) at 300° C., overall silicon utilization was comparable to 100% hydrogen chloride feed reaction.

(c) at 300° C., mixed feed methyl chloride: hydrogen chloride resulted in higher silicon utilization to form methylchlorosilanes than 100% methyl chloride reaction at the same temperature.

(d) the reaction at 200° C. sharply suppressed the alkylation reaction, that is, methyl chloride and silicon, but resulted in a sacrifice in overall silicon utilization.

(e) inclusion of hydrogen chloride results in marked increases in E/F of methylchlorosilane product.

(f) residue formation increases as reaction temperature is lowered.

From the foregoing data, it is clear that hydrogen chloride and methyl chloride react with silicon-copper mixes to yield trichlorosilane and silicon tetrachloride at selected lower temperatures.

In accordance with at least some of the objects of the present invention, a process has been demonstrated for the preparation of trichlorosilane in substantial quantities by means of a hydrochlorination reaction carried out under selected temperature conditions which suppress the alkylation reaction between methyl chloride and silicon. By modification of reaction temperature and by careful control of temperature, enhanced yields of trichlorosilane and silicon tetrachloride were achieved. Furthermore, reaction in the co-feed mode, that is, feeding both hydrogen chloride and methyl chloride in the presence of silicon at low temperatures in the range of about 200° C. to about 300° C. demonstrated an ability to suppress, selectively, the methylchlorosilane reaction, that is, an alkylation reaction, while continuing hydrochlorination of the silicon.

Although the process was not carried out using fresh or virgin silicon, the process of the present invention may be generalized to the utilization of such species, and fresh or virgin silicon can be reacted with gaseous alkyl halide and gaseous hydrogen halide at a selected temperature between about 200° C. and about 350° C. at which alkylation of the silicon is inhibited and at which hydrohalogenation of the silicon occurs, whereby the silicon reacts with gaseous alkyl halide and gaseous hydrogen halide at the selected temperature to produce improved yields of monohydrogentrihalosilanes.

While the present invention has been described in detail with particular reference to certain preferred embodiments thereof, it will be understood that variations and modifications can be effected within the spirit and scope of the invention.

What is claimed is:

1. A process for preparing monohydrogen trihalosilane from the residual silicon obtained from the preparation of organohalosilanes by a metal-catalyzed direct process, comprising, contacting the residual silicon simultaneously with gaseous hydrogen halide and with gaseous alkyl halide to form a residual silicon contact mass and heating the residual silicon contact mass at a temperature less than the temperature at which substantial alkylation of the residual silicon contact mass occurs, whereby the residual silicon reacts at said temperature to produce reaction products containing monohydrogentrihalosilane.

2. The process of claim 1 wherein gaseous hydrogen halide and gaseous alkyl halide contact a fluidized bed of the residual silicon.

3. The process of claim 1 wherein the gaseous alkyl halide is selected from the group consisting of the chloride, bromide, iodide or fluoride of an alkyl group having from 1 to 4 carbon atoms.

4. The process of claim 1 wherein the gaseous hydrogen halide is selected from the group consisting of hydrogen chloride, hydrogen bromide, hydrogen iodide and hydrogen fluoride.

5. The process of claims 1 or 2 wherein the gaseous hydrogen halide is hydrogen chloride; the gaseous alkyl halide is methyl chloride; and the monohydrogentrihalosilane is monohydrogentrichlorosilane.

6. The process of claim 1 wherein the molar ratio of alkyl halide to hydrogen halide is in the range of about 6:1 to about 1:6.

7. The process of claims 1 or 2 wherein the residual silicon contact mass is heated selectively at a temperature of about 200° C. to about 350° C.

8. The process of claim 1 further comprising collecting the reaction products and separating the monohydrogentrihalosilane therefrom.

9. A process for preparing monohydrogentrichlorosilane from the residual silicon obtained from the preparation of organochlorosilanes by the direct process comprising, providing gaseous methyl chloride and gaseous hydrogen chloride to a fluidized bed of the residual silicon in a molar ratio of methyl chloride:hydrogen chloride in the range of about 6:1 to about 1:6 and heating the fluidized bed of residual silicon at a temperature between about 200° C. and 300° C., the temperature being less than the temperature at which substantial alkylation of the residual silicon occurs, to produce a product containing substantial amounts of monohydrogentrihalosilane and silicon tetrachloride.

10. The process of claim 9 wherein the molar ratio of methyl chloride:hydrogen chloride is between about 3:1 and about 1:3.

11. The process of claim 9 wherein the residual silicon comprises silicon fines collected from a secondary cyclone used to separate spent silicon fines obtained from the direct process preparation of organochlorosilanes.

12. The process of claim 9 further comprising collecting the product and separating the monohydrogentrichlorosilane therefrom.

13. The process of claim 9 wherein the molar ratio of methyl chloride:hydrogen chloride is about 3:1; the temperature is about 200° C. to about 250° C.; and the predominant product is monohydrogentrichlorosilane.

14. A method for improving the amount of monohydrogentrihalosilane obtained from the reaction of silicon with alkyl halide in the metal-catalyzed direct process comprising, contacting the silicon simultaneously with gaseous alkyl halide and with gaseous hydrogen halide to form a silicon contact mass; selecting a temperature between about 200° C. and about 350° C. at which alkylation of the silicon contact mass is inhibited and at which hydrohalogenation of the silicon contact mass occurs; and heating the silicon contact mass at the selected temperature, whereby the silicon reacts with the gaseous alkyl halide and the gaseous hydrogen halide at the selected temperature to produce improved yields of monohydrogentrihalosilane.

15. A method for improving the amount of monohydrogentrihalosilane obtained from the reaction of residual silicon obtained from the preparation of organohalosilanes by a metal-catalyzed direct process, comprising, contacting the residual silicon simultaneously with gaseous alkyl halide and with gaseous hydrogen halide to form a residual silicon contact mass; selecting a temperature between about 200° C. and about 350° C. at which alkylation of the residual silicon contact mass is inhibited and at which hydrohalogenation of the residual silicon contact mass occurs; and heating the residual silicon contact mass at the selected temperature, whereby the silicon in the residual silicon contact mass reacts with the gaseous alkyl halide and the gaseous hydrogen halide at the selected temperature to produce improved yields of monohydrogentrihalosilane.

16. The method of claims 14 or 15 wherein the gaseous alkyl halide and gaseous hydrogen halide contact a fluidized bed of the silicon or residual silicon.

17. The method of claims 14 or 15 wherein the gaseous alkyl halide is selected from the group consisting of the chloride, bromide, iodide or fluoride of an alkyl group having from 1 to 4 carbon atoms.

18. The process of claims 14 or 15 wherein the gaseous hydrogen halide is selected from the group consisting of hydrogen chloride, hydrogen bromide, hydrogen iodide and hydrogen fluoride.

19. The process of claims 14 or 15 wherein the gaseous hydrogen halide is hydrogen chloride; the gaseous alkyl halide is methyl chloride; and the monohydrogentrihalosilane is monohydrogentrichlorosilane.

20. The process of claims 14 or 15 wherein the molar ratio of alkyl halide to hydrogen halide is in the range of about 6:1 to about 1:6.

21. The process of claims 14 or 15 wherein the molar ratio of alkyl halide to hydrogen halide is in the range of about 3:1 to about 1:3.

22. The process of claims 14 or 15 wherein the gaseous hydrogen halide is hydrogen chloride; the gaseous alkyl halide is methyl chloride; the alkyl halide:hydrogen halide molar ratio is in the range of about 3:1; and the selected temperature is about 200° C. to about 250° C., whereby the silicon reacts with the methyl chloride and the hydrogen chloride to produce a product comprising substantially monohydrogentrichlorosilane.

23. The process of claims 14 or 15 further comprising collecting a reaction product and separating the monohydrogentrihalosilane therefrom.

* * * * *